(12) United States Patent
Su et al.

(10) Patent No.: US 9,695,472 B2
(45) Date of Patent: *Jul. 4, 2017

(54) SENSOR ARRAYS AND NUCLEIC ACID SEQUENCING APPLICATIONS

(75) Inventors: Xing Su, Cupertino, CA (US); Kai Wu, Mountain View, CA (US)

(73) Assignee: INTEL CORPORATION, Santa Clara, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/950,729

(22) Filed: Nov. 19, 2010

(65) Prior Publication Data

US 2011/0065588 A1    Mar. 17, 2011

Related U.S. Application Data

(63) Continuation-in-part of application No. 11/226,696, filed on Sep. 13, 2005, which is a continuation-in-part of application No. 11/073,160, filed on Mar. 4, 2005, now abandoned.

(51) Int. Cl.
  *C12Q 1/68* (2006.01)
  *B82Y 30/00* (2011.01)
  *B01L 3/00* (2006.01)
  *G01N 27/414* (2006.01)

(52) U.S. Cl.
  CPC ........... *C12Q 1/6874* (2013.01); *B82Y 30/00* (2013.01); *B01J 2219/0063* (2013.01); *B01J 2219/00317* (2013.01); *B01J 2219/00511* (2013.01); *B01J 2219/00605* (2013.01); *B01J 2219/00612* (2013.01); *B01J 2219/00621* (2013.01); *B01J 2219/00626* (2013.01); *B01J 2219/00641* (2013.01); *B01J 2219/00722* (2013.01); *B01L 3/5085* (2013.01); *C12Q 1/6825* (2013.01); *G01N 27/414* (2013.01)

(58) Field of Classification Search
  None
  See application file for complete search history.

(56) References Cited

U.S. PATENT DOCUMENTS 5,795,714 A     8/1998  Cantor et al.
5,849,487 A  *  12/1998  Hase et al. ................... 435/6.12
5,866,323 A     2/1999  Markowitz et al.
(Continued)

FOREIGN PATENT DOCUMENTS

WO    WO 03/054225 A2  *  7/2003  ............... C12Q 1/68

OTHER PUBLICATIONS

Description of Therminator polymerase from neb.com [retrieved on Sep. 13, 2012]. Retrieved from the Internet: <URL: www.neb.com/nebecomm/products/productM0266.asp>.*

(Continued)

*Primary Examiner* — Robert T Crow
(74) *Attorney, Agent, or Firm* — Pillsbury Winthrop Shaw Pittman LLP

(57) ABSTRACT

Embodiments of the present invention provide devices methods for sequencing DNA using arrays of reaction regions containing electronic sensors to monitor changes in solutions contained in the reaction regions. Test and fill reaction schemes are disclosed that allow DNA to be sequenced. By sequencing DNA using parallel reactions contained in large arrays, DNA can be rapidly sequenced.

14 Claims, 11 Drawing Sheets

(56) References Cited

U.S. PATENT DOCUMENTS

| | | | |
|---|---|---|---|
| 6,159,693 A * | 12/2000 | Shultz | C12Q 1/04 435/17 |
| 6,232,075 B1 * | 5/2001 | Williams | 435/6.12 |
| 6,613,523 B2 * | 9/2003 | Fischer | 435/6.12 |
| 6,682,887 B1 | 1/2004 | Singh | |
| 6,952,651 B2 | 10/2005 | Su | |
| 6,972,173 B2 | 12/2005 | Su et al. | |
| 7,005,264 B2 | 2/2006 | Su et al. | |
| 7,033,762 B2 | 4/2006 | Nelson et al. | |
| 7,238,477 B2 | 7/2007 | Su et al. | |
| 7,476,501 B2 | 1/2009 | Chan et al. | |
| 8,563,240 B2 | 10/2013 | Su et al. | |
| 9,040,237 B2 | 5/2015 | Koo et al. | |
| 2002/0004204 A1 | 1/2002 | O'Keefe | |
| 2002/0042388 A1 | 4/2002 | Cooper et al. | |
| 2002/0127736 A1 | 9/2002 | Chou et al. | |
| 2002/0187515 A1 | 12/2002 | Chee et al. | |
| 2003/0096253 A1 | 5/2003 | Nelson et al. | |
| 2003/0113737 A1 | 6/2003 | Pedersen | |
| 2003/0116723 A1 | 6/2003 | Yoshida | |
| 2003/0152985 A1 * | 8/2003 | Pourmand et al. | 435/6 |
| 2003/0155942 A1 * | 8/2003 | Thewes | 324/769 |
| 2003/0215816 A1 | 11/2003 | Sundararajan et al. | |
| 2003/0215842 A1 | 11/2003 | Sledziewski et al. | |
| 2003/0215862 A1 * | 11/2003 | Parce et al. | 435/6 |
| 2004/0005572 A1 | 1/2004 | Rosner et al. | |
| 2004/0067530 A1 * | 4/2004 | Gruner | 435/7.1 |
| 2004/0110208 A1 | 6/2004 | Chan et al. | |
| 2005/0019784 A1 | 1/2005 | Su et al. | |
| 2005/0026163 A1 | 2/2005 | Sundararajan et al. | |
| 2005/0106587 A1 * | 5/2005 | Klapproth et al. | 435/6 |
| 2005/0186576 A1 | 8/2005 | Chan et al. | |
| 2006/0029969 A1 | 2/2006 | Su et al. | |
| 2006/0068440 A1 | 3/2006 | Chan et al. | |
| 2006/0141485 A1 | 6/2006 | Su | |
| 2007/0231790 A1 | 10/2007 | Su | |
| 2007/0231795 A1 | 10/2007 | Su | |
| 2008/0032297 A1 | 2/2008 | Su et al. | |
| 2008/0160630 A1 | 7/2008 | Liu | |
| 2009/0170716 A1 | 7/2009 | Su et al. | |
| 2010/0267013 A1 | 10/2010 | Su et al. | |
| 2010/0330553 A1 | 12/2010 | Su et al. | |

OTHER PUBLICATIONS

Gardner et al, Nuc. Acids. Res., vol. 30, pp. 605-613 (2002).*

Elibol, et al., "Nanoscale thickness double-gated field effect silicon sensors for sensitive pH detection in fluid", Applied Physics Letters 92, May 15, 2008, pp. 193904-1 to 193904-3.

Stephens S. W. Yeung et al., "Electrochemical Real-Time Polymerase Chain Reaction," Journal of the Electrochemical Society, 2006, pp. 13374-13375, vol. 128, No. 41, S1-S2.

M. Gabig-Ciminska, et al., "Electric Chips for Rapid Detection and Quantification of Nucleic Acids," Biosensors and Bioelectronics, 2004, pp. 537-546, vol. 19.

Kling, Jim, "Ultrafast DNA sequencing", Nature Biotechnology, Dec. 2003, v. 21, No. 12, pp. 1425-1427.

Eilbol, Oguz H. et al., "Localized heating and thermal characterization of high electrical resistivity silicon-on-insulator sensors using nematic liquid crystals" Applied Physics Letters, 93, 131908, Sep. 30, 2008.

Rolka, David et al., "Integration of a Capacitive EIS Sensor into a FIA System for pH and Penicillin Determination", Sensors, (2004) pp. 84-94.

Janicki, Marcin et al., "Ion Sensitive Field Effect Transistor Modelling for Multidomain Simulation Purposes", Microelectronics, Journal, 35 (2004) pp. 831-840.

Ronaghi, Mostafa et al., "DNA Sequencing: A Sequencing Method Based on Real-Time Pyrophosphate", Science, vol. 281, No. 5375 (1998) pp. 363-365.

Fritz, Jurgen et al., "Electronic detection of DNA by its intrinsic molecular charge", Proc. Nat. Acad. Sci. USA, Oct. 29, 2002, vol. 99, No. 22, pp. 14142-14146.

Chen, Robert J. et al., "Noncovalent functionalization of carbon nanotubes for highly specific electronic biosensors", Proc. Nat. Acad, Sci. USA, dated Apr. 29, 2003, vol. 100 No. 9, pp. 4984-4989.

Gao, Guangxia et al., "Conferring RNA polymerase Activity to a DNA polymerase: A single residue in reverse transcriptase controls substrate selection," Proc. Natl. Acad. Sci. USA, Biochemistry, vol. 94, pp. 407-411, Jan. 1997.

Delucia Angela M. et al., "An error-prone family Y DNA polymerase (Din B homolog from Sulfolobus solfataricus) uses a 'stericgate' residue for discrimination against ribonucleotides", Nucleic Acids Research, vol. 31, No. 14, (2003), pp. 4129-4137.

Star, Alexander et al., "Electronic Detection of Specific Protein Binding Using Nanotube FET Devices," Nano Letters, vol. 3, No. 4, Mar. 5, 2003, pp. 459-463.

U.S. Non-Final Office Action issued Oct. 16, 2015 in corresponding U.S. Appl. No. 14/719,192 (25 pages).

Final Office Action issued on Mar. 4, 2016 in U.S. Appl. No. 14/719,192 (28 pages).

* cited by examiner

SENSOR ARRAYS AND NUCLEIC ACID SEQUENCING APPLICATIONS

CROSS-REFERENCE TO RELATED APPLICATIONS

The present continuation-in-part application claims the benefit of U.S. application Ser. No. 11/226,696, filed Sep. 13, 2005, which itself claims the benefit of U.S. application Ser. No. 11/073,160, filed Mar. 4, 2005, the disclosures of which are incorporated herein by reference. An additional related application is U.S. patent application Ser. No. 12/823,995, entitled "Nucleotides and Oligonucleotides for Nucleic Acid Sequencing," filed Jun. 25, 2010 the disclosure of which is incorporated herein by reference.

BACKGROUND OF THE INVENTION

Field of the Invention

The embodiments of the present invention relate generally to methods and devices for nucleic acid sequence detection.

Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, and sickle cell anemia. Determination of the entire three billion nucleotide sequence of the human genome has provided a foundation for identifying the genetic basis of such diseases. An determination of the sequence of the human genome required years to accomplish using traditional technologies. The need for nucleic acid sequence information also exists in research, environmental protection, food safety, biodefense, and clinical applications, such as for example, pathogen detection (the detection of the presence or absence of pathogens or their genetic varients).

Thus, because DNA sequencing is an important technology for applications in bioscience and personalized medicine, such as, for example, the analysis of genetic information content for an organism, tools that allow for faster and or more reliable sequence determination are valuable. Applications such as, for example, population-based biodiversity projects, disease detection, prediction of effectiveness of drugs, and genotyping using single-nucleotide polymorphisms, stimulate the need for simple and robust methods for sequencing short lengths of nucleic acids (such as, for example, those containing 1-20 bases). Sequencing methods that provide increased accuracy and or robustness, decreased need for analysis sample, and or high throughput are valuable analytical and biomedical tools.

BRIEF DESCRIPTION OF THE FIGURES

The following drawings are included to further demonstrate certain aspects of the disclosed embodiments of the invention.

DETAILED DESCRIPTION OF THE INVENTION

Embodiments of the present invention provide devices and methods for sequencing nucleic acids and nucleic acid detection. In general, nucleic acids useful in the present invention include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). Additionally, non-naturally occurring nucleic acids that are susceptible to enzymatic synthesis and degredation may be used in embodiments of the present invention.

Methods for preparing and isolating various forms of nucleic acids are known. See for example, Berger and Kimmel, eds., *Guide to Molecular Cloning Techniques*, Academic Press, New York, N.Y. (1987); and Sambrook, Fritsch and Maniatis, eds., *Molecular Cloning: A Laboratory Manual, 2nd Ed.*, Cold Spring Harbor Press, Cold Spring Harbor, N.Y. (1989). However, embodiments of the present invention are not limited to a particular method for the preparation of nucleic acids.

Figure 1:
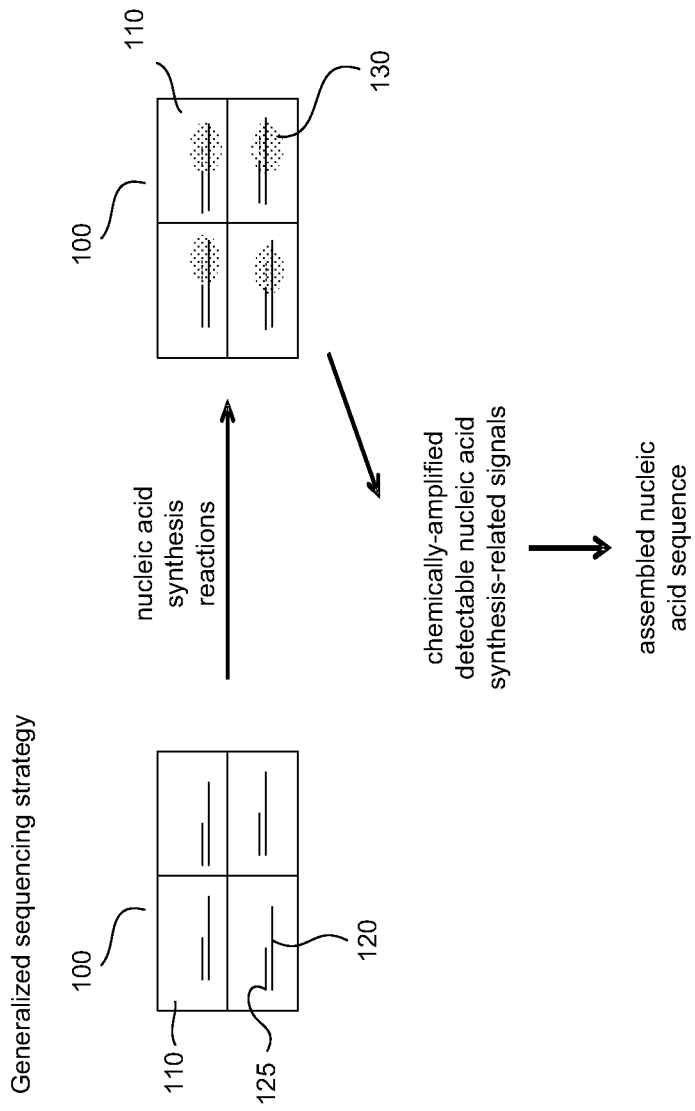
FIG. 1 shows an outline for a general nucleic acid sequencing strategy using test and fill (TAF) reactions and a sensor array to detect the generation of reaction products.

Referring now to FIG. 1, an array of electronic sensors 100, such as, for example, field-effect-transistor (FET) sensors, having reaction sensor regions 110 (reaction regions) and immobilized DNA molecules 120 is depicted. A primer molecule 125 is hybridized to the immobilized DNA molecules 120. Sensors can also be impedance meters, for example. One DNA molecule to be sequenced 120 is immobilized per sensor region 110 in this example. Before sequencing a sample of DNA, overlapped DNA fragments are immobilized randomly on the array so that statistically one DNA molecule occupies the reaction region 110 of a sensor. A sample of DNA can be fragmented into smaller polymeric molecules using, for example, restriction enzymes or mechanical forces (shearing). Test and fill (TAF) reactions are performed and amplified chemical products 130 are created in the reaction regions 110. Chemical products 130 are amplified through repeated cycles of matching a base (or nucleotide, used interchangeably here) in a DNA template molecule to be sequenced with a testing base, filling the next available position on the growing DNA strand with the matching base, and then removing the newly added matching base. The identified base position is then filled with a nuclease resistant base, and the reaction is repeated to determine a matching base for the next available position on the DNA strand to be sequenced. In this example, the amplified chemical products 130 are detected electronically and sequence data for the immobilized DNA molecules is assembled. Amplified chemical products 130 in a reaction region 110, such as, for example, a gate or an extended gate of a FET, change the ionic conditions or pH of the region and thus alter the current flow between the source and the drain. In the case in which sensors are electrodes, changes in chemical products change the capacitance and or resistance of the sensor electrodes. Reaction conditions and their corresponding positions and electronic signals are recorded and analyzed with a computer and software.

Figure 2:
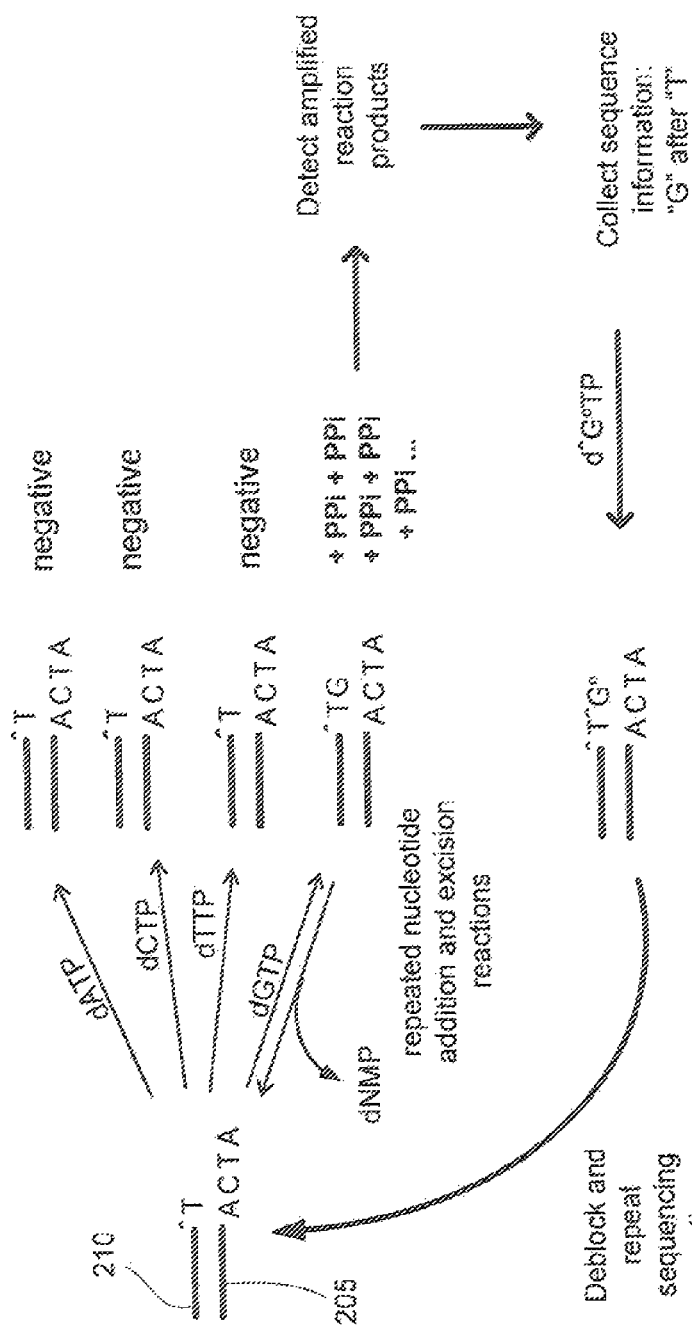
FIG. 2 shows a general scheme for a test and fill sequencing reaction.

Referring now to FIG. 2, an exemplary test and fill chemical reaction is shown. In this reaction, a portion of a DNA molecule 205 is sequenced through testing with four nucleotides. In one embodiment, regular dNTPs (deoxynucleoside triphosphates) are used and a determination is made as to which one is incorporated into the primed DNA molecule. In further embodiments, non-natural dNTPs are used to determine sequence information through incorporation and excision reactions. In FIG. 2, a DNA molecule to be sequenced 205 is primed with a primer 210 that is terminated with an exonuclease resistant nucleotide which, in this example, is a thymine (nuclease resistance being indicated in FIG. 2 with a "^"). The chemical products resulting from the incorporation of a complementary dNTP (a deoxynucleoside triphosphate, e.g., dATP (deoxyadenosine triphosphate), dCTP (deoxycytidine triphosphate), dGTP (deoxyguanosine triphosphate), or dTTP (deoxythymidine triphosphate), for example) or dNTP analog, complementary to a base of the nucleic acid strand to be sequenced 205 are amplified through the repeated addition and excision of the next complementary nucleoside onto the priming sequence 210. In general, a test reaction comprises a polymerase, an exonuclease, a deoxynucleoside triphosphate (dATP (deoxyadenosine triphosphate), dCTP (deoxycytidine triphosphate), dGMP (deoxyguanosine triphosphate), dTMP (deoxythymidine triphosphate)) or a nucleoside tetra- or pentaphosphate), and optionally a pyrophosphatase. A nucleoside is incorporated into the primed growing DNA molecule that is terminated with a nuclease resistant base through the action of a polymerase enzyme. Typical useful polymerase enzymes include DNA polymerases with or without 3' to 5' exonuclease activities, such as for example, *E. coli* DNA polymerase I, Klenow fragment of *E. Coli* DNA polymerase I, exo-minus Klenow fragment of *E. Coli* DNA polymerase I(Klenow exo- or exonuclease free klenow polymerase), Therminator DNA polymerase, reverse transcriptase, Taq DNA polymerase, Vent DNA polymerase (all available from New England Biolabs, Inc., Beverly, Mass.), T4 DNA polymerase, and Sequenase (both available from USB, Cleveland, Ohio). Thus where there is a cytosine on the strand to be sequenced, a guanine will be incorporated, where there is a thymidine, an adenine will be incorporated, and vice versa. If the nucleoside triphosphate is incorporated into the growing strand in the test reaction, then pyrophosphate (PPi) is released. The pyrophosphate can optionally be degraded into two inorganic phosphates through ionic dissociation caused by water and catalyzed by pyrophosphatase. In an amplification reaction, an exonuclease is used to remove the incorporated nucleoside monophosphate $(NMP^{-2})$, allowing another nucleoside triphosphate to be incorporated and a PPi to be released. Repetition of these reactions provides linear amplification of PPi and or inorganic phosphates. Thus, a positive test reaction indicates that the base on the template DNA strand to be sequenced immediately after the priming base (the 3' base) of the primer strand is complementary to the test base introduced into the reaction. To sequence the next base on the template, the first identified base on the primer strand is filled or replaced with a nuclease-resistant nucleotide that then becomes the priming base for the test reaction. Nuclease-resistant nucleotides can be ribonucleotides or other modified nucleotides. A variety of polymerases are available that can incorporate ribonucleotides or modified nucleotides into DNA, such as for example, the commercially available Therminator DNA polymerases (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant bases that can be incorporated into growing DNA strands but that are resistant to digestion by exonucleases (such as the 3' to 5' exonuclease active DNA polymerases or exonuclease I or III) include alpha phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases, but the ribonucleotide bases are resistant to digestion by exonucleases, such as exonucleases I or exonuclease III (available from New England Biolabs). Exemplary nucleases that cannot digest these resistant bases include exonuclease I, nuclease III, and 3' to 5' exonuclease active DNA polymerases.

In FIG. 2, to sequence the next base on the template, the first identified base on the primer strand 210 is filled or replaced with an identified nuclease-resistant nucleoside that then becomes the priming base for the next test reaction after deblocking. Optionally, the nucleoside is nuclease-resistant blocking nucleoside (3' blocking is indicated with a"°"" in FIG. 2). In general, blocking nucleosides prevent further nucleic acid synthesis by reversibly blocking the addition of a nucleic acid to the end of the nucleic acid molecule. Nuclease-resistant blocking nucleosides are, for example, ribonucleosides or other modified nucleosides and are described more fully herein. A variety of polymerases are available that can incorporate ribonucleotides or modified nucleosides into DNA, such as for example, the commercially available Therminator DNA polymerases (available from New England Biolabs, Inc., Ipswitch, Mass.). See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant bases include alpha-phosphorothioate nucleosides having different chiralities, and exemplary nucleases that cannot digest the specific chiral isomer of the phosphorothioate bond include polymerase associated exonuclease such as the exonuclease activity of T4 or T7 Polymerase (which can not digest S-chiral conformation of the phosphorothioate bond) or a 3' to 5' exonuclease with chiral specificity (such as Exonuclease III which would not digest R-chiral conformation of phosphorothioate bond). Some polymerase enzymes possess intrinsic exonuclease activity therefore it is not always necessary to use two different enzymes for the addition and excision reactions. Reactions in which no significant amount of product is detected indicate that the test reaction provided a nucleotide that was not complementary to the next base of the nucleic acid to be sequenced. After addition of the next known complementary nucleotide to the primer 210, the primer 210 is deblocked through removal of the 3' blocking group and the identity of the next complementary nucleotide is determined by repeating the test reactions as described above.

Reversible terminators that have been modified at the 3' position with, for example, 3'-azidomethyl or 3'-allyl, are cleaved chemically to deblock the nucleotide, using for example, TCEP (tricarboxylethylphosphine) for 3'-azidomethyl and aqueous Pd-based catalyst to remove 3'-allyl group, and 3'O-nitrobenzyl blocking groups are cleaved photochemically.

Figure 3:
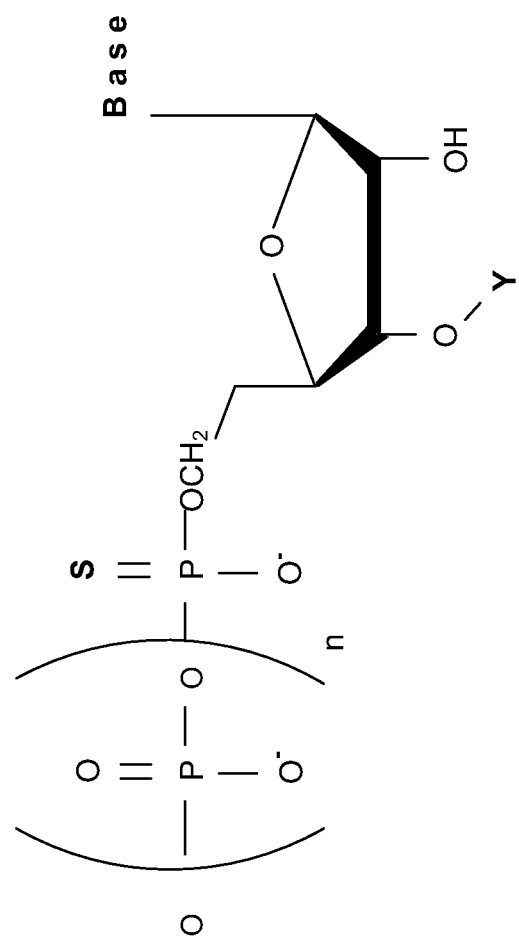
FIG. 3 shows nucleotides that are useful in sequencing reactions.

In an embodiment of the invention, the nuclease resistant nucleoside is the molecule shown in FIG. 3, an alpha-thiophosphate nucleoside. In FIG. 3, the base, B, is adenine (A), cytosine (C), guanine (G), thymine (T), uracil (U), or an analog thereof, such as, for example, a modified base, a hydrophobic base analog, such as for example, 2,4-difluoro-5-toluene (Kool E. T., *Acc. Chem. Res.*, 35, 936-943 (2002)), universal base (3-nitropyrrole or 5-nitroindole) or isoguanine and isocytosine; n is a number between and including 2 and 4, and Y is H, azidomethyl, allyl, acetyl, or O-nitrobenzyl. In embodiments of the invention, the alpha-thiophosphate nucleoside is the R or the S enantiomer of the thiophosphate group. The polyphosphate nucleoside of FIG. 3 is optionally a blocking nucleoside, and is not a blocking nucleotide when Y is H. Optionally, the nucleotide of FIG. 3 is provided as an acid or a neutral salt that is compatible with nucleic acid synthesis reactions, such as for example, as a $H^+$, $Na^+$, $K^+$, triethylamine, or tributlyamine.

According to embodiments of the invention, the primer molecule that is hybridized to the nucleic acid molecule to be sequenced is terminated with a nucleoside as shown in FIG. 3 that is either blocking or not blocking. Sequencing reactions involving nucleoside polyphosphate incorporation and excision as described herein are performed. The one or more enzymes used to add and excise a next complementary nucleoside polyphosphate are not able to digest the alpha-thiophosphate nucleoside that terminates the primer molecule. In an embodiment, the alpha-thiophosphate nucleoside that terminates the primer molecule is the R enantiomer of the thiophosphate group. An exemplary enzyme that cannot digest alpha-thiophosphate nucleosides is exonuclease III (Exo III). More specifically, Exo III cannot digest the R enantiomer of the thiophosphate group. In an embodiment of the invention, a combination of Klenow (exo-) (a polymerase enzyme lacking the 3' to 5' exonuclease activity) and Exo III (an exonuclease) are used in sequencing reactions in which a nucleoside polyphosphate is incorporated and excised repeatedly. An enzyme capable of incorporating an alpha-thiolated nucleoside according to FIG. 3 is Therminator II or III or γ polymerase (ThII or Th III Pol. or Th-γ Pol.). After the identity of a base of the molecule to be sequenced is determined, the position is filled with a complementary alpha-thiolated nucleoside oligophosphate (tri-, tetra-, or penta-phosphate).

Figure 4:
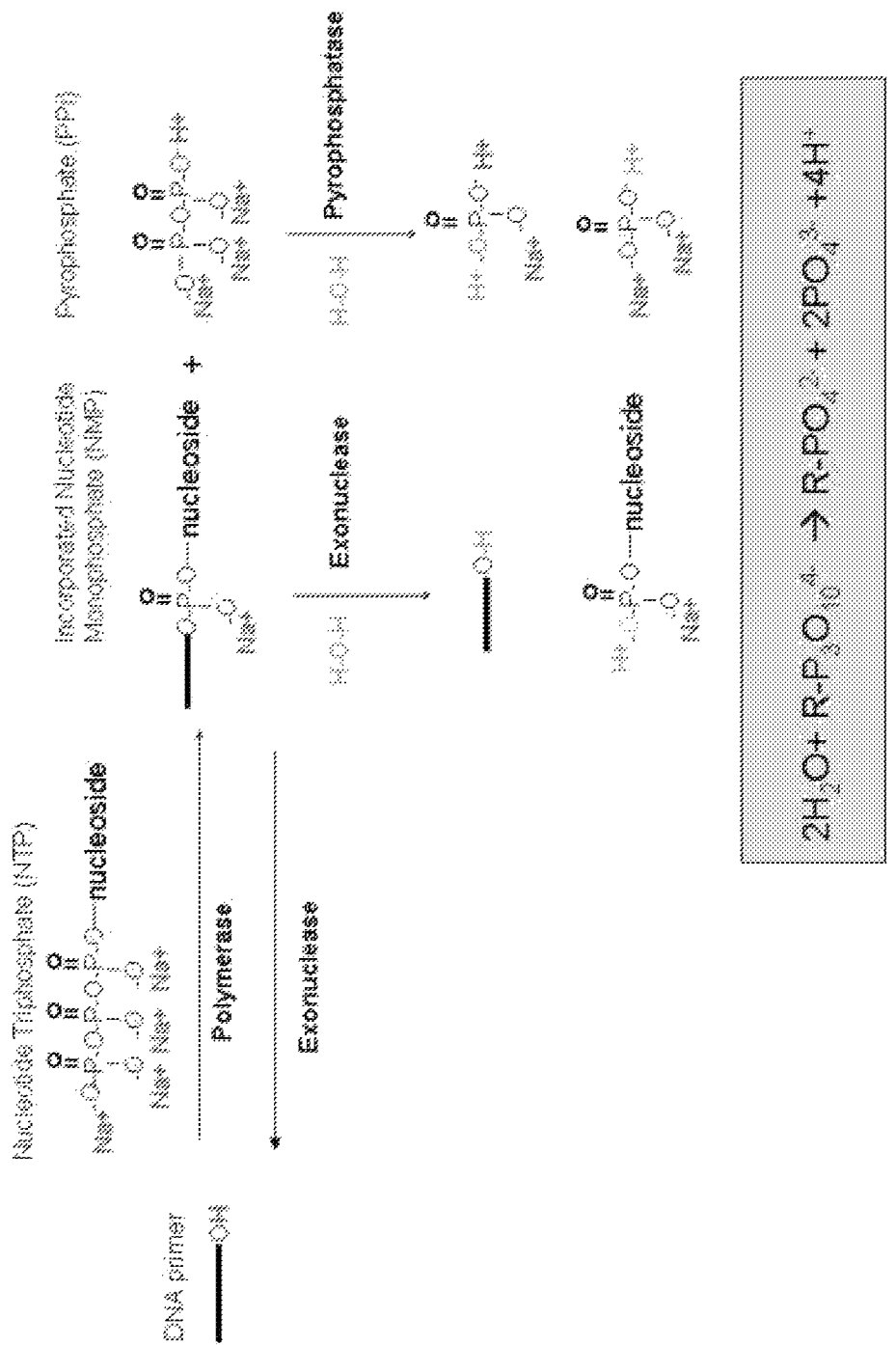
FIG. 4 shows a schematic of a method for achieving chemical signal amplification in a test and fill sequencing reaction.

Referring now to FIG. 4, a reaction that provides chemical signal amplification for nucleotide incorporation into DNA is shown. A test reaction for a single base position in a DNA molecule can also be considered to be a chemical amplification reaction in which many dNTP molecules are converted into pyrophosphate and dNMP. In this reaction, a pyrophosphate can be further converted into two phosphates by, for example, pyrophosphatase and spontaneous hydrolysation. Thus, as can be seen in FIG. 3, after incorporation of a nucleotide into a primed DNA molecule through, for example, the action of a polymerase enzyme, the nucleotide can then be deleted through, for example, the action of an exonuclease enzyme. These reactions can be repeated many times for the same incorporation event on a DNA molecule, resulting in the consumption of many nucleotide triphosphates and the generation of many molecules of pyrophosphate and/or phosphate. The generation of pyrophosphate and/or phosphate can affect the local pH (by providing a net proton ($H^+$) increase) and the ionic strength of the reaction solution. Since each dNTP has four ionizable groups and its products have a total of eight ionizable groups, a net increase of four ionizable groups and 4 protons ($H^+$) is realized through the incorporation-deletion reaction cycle. The incorporation-deletion reaction cycle can be repeated many times as long as a matched dNTP is present. For example, for ten rounds of incorporation-deletion cycles, assuming a reaction cavity having the dimensions of 100 nm in diameter and 100 nm in depth, the change in ionizable groups would be equal to 85 µm of monovalent ions. The increase in acidity and/or ionic strength can be sensed electronically, such as for example, with a reaction cavity coupled to a FET sensor.

Figure 5:
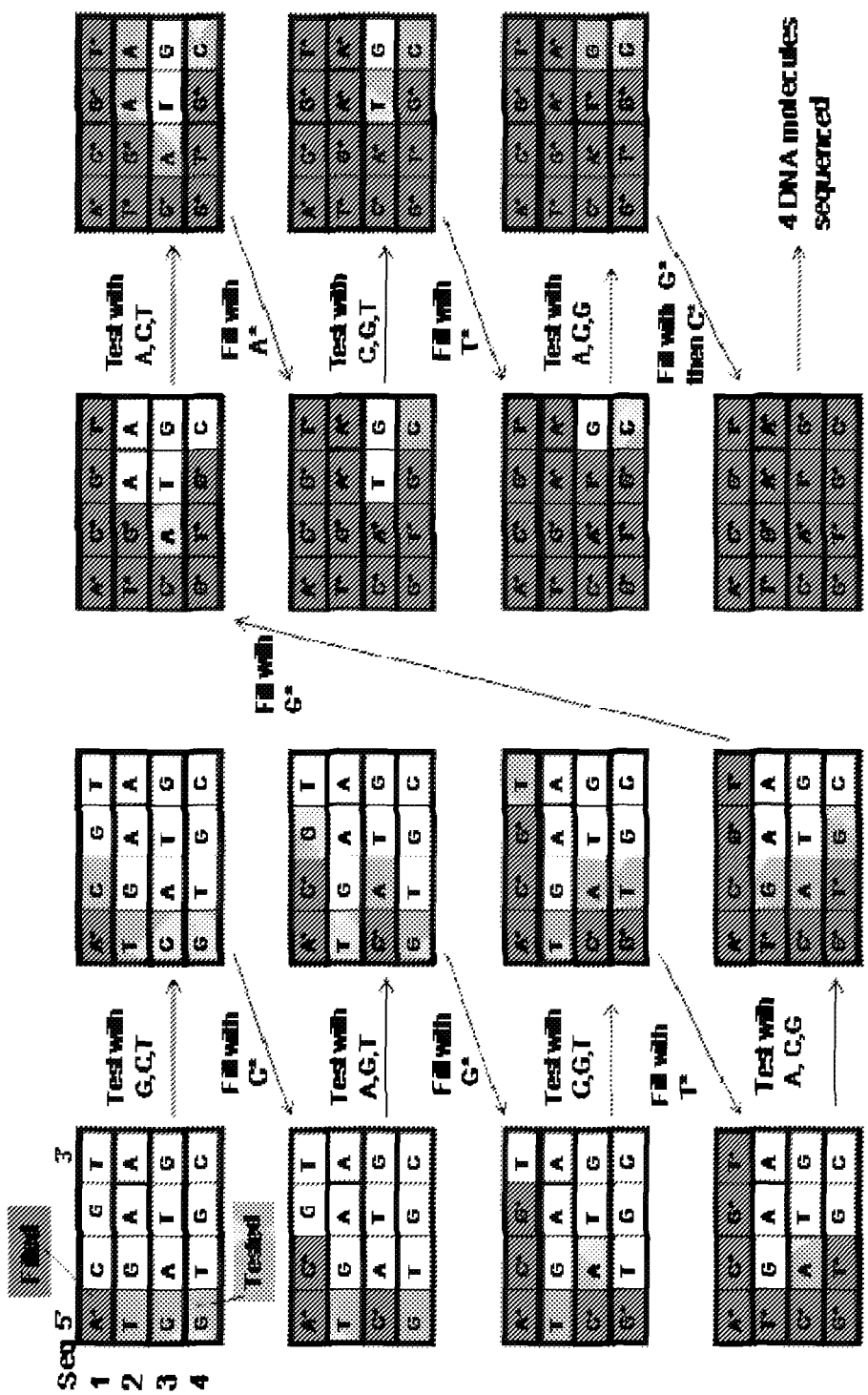
FIG. 5 demonstrates a method for parallel sequencing of nucleic acids using the test and fill sequencing principle.

FIG. 5 shows how parallel sequencing of more than one DNA molecule can be accomplished according to embodiments of the present invention. In FIG. 4, four DNA molecules to be sequenced are placed in four separate sensor cells. After each fill reaction with a nuclease-resistant nucleotide, for example A (indicated in FIG. 5 as A*), a test reaction is carried out with three other regular nucleotides, such as for example, C, G, and T, separately and sequentially (it is not necessary that the nucleotides be tested in any particular order) to identify the next complementary nucleotide (base) for each DNA molecule that is being sequenced. The next filling nuclease resistant nucleotide should be the one identified in the test reaction as the next complementary nucleotide. These reactions are then repeated to sequence the DNA. Thus, sequence information for each DNA molecule is obtained from the results of positive test reactions for sequences without repetitive bases. Sequence information for repeated nucleotides is determined based on the amplitude of the measured chemical and/or electronic signals. For sequences having repetitive bases, more phosphates are generated per test reaction as compared to a single base, therefore the quantity difference can be used to determine the number of bases in a repetitive sequence. Alternatively, a stronger exonuclease activity can be used so that the nucleotide deletion rate is much higher than the nucleotide insertion (extension) rate in the test reaction, and then a mixture of regular dNTP and nuclease resistant nucleotides (NRN) is used for a fill reaction with a polymerase and a strong exonuclease. Redundant reactions can optionally be used to increase accuracy.

Figure 6:
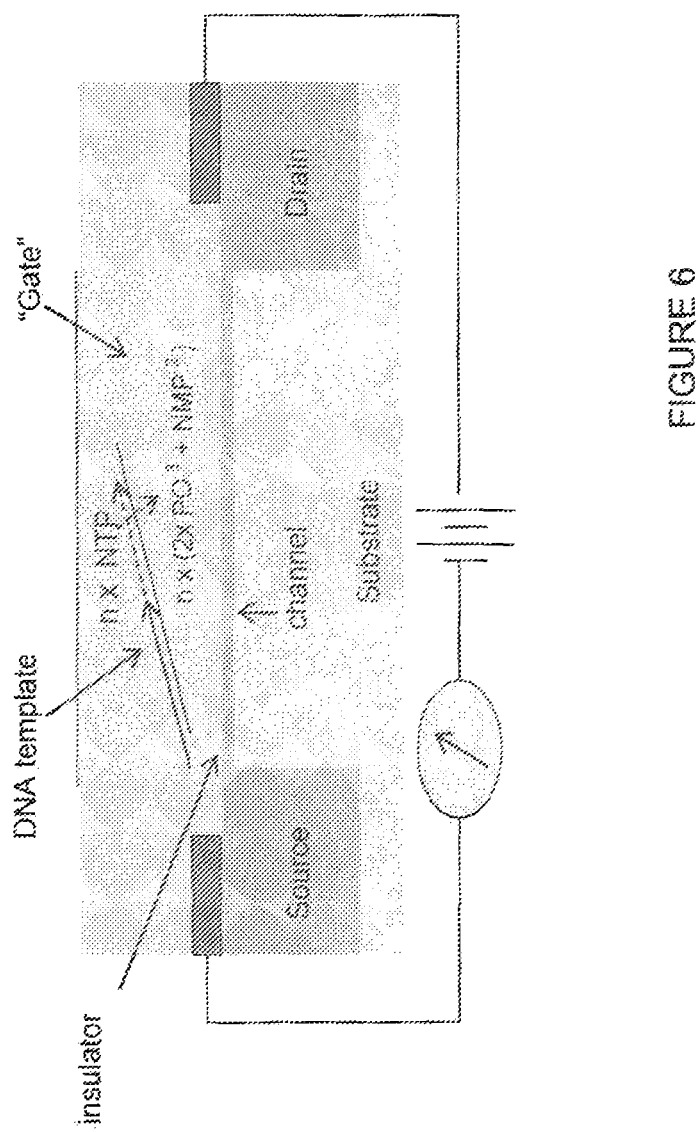
FIG. 6 is a schematic of device employing a field effect transistor that can be used for analyzing a solution-based nucleic acid sequencing reaction.

Referring now to FIG. 6, a sensor cell according to an embodiment of the present invention is shown. In the cell the amplified chemical signals from the TAF reactions can be converted into an electronic signal by an electronic sensor. For example, the sensor can be a P-type FET, a N-type FET, or a carbon nanotube transistor. See, for example, Janicki, M., Daniel, M., Szermer, M., Napieralski, A., *Microelectronics Journal*, 35, 831-840 (2004) and Rolka, D., Poghossian, A., Schoning, M., *Sensors*, 4, 84-94 (2004). In one embodiment, each sensor has a nano-sized reaction cavity and a semiconductor transistor that are separated by an insulating layer. The insulating layer can, for example, be made from silicon oxide, silicon nitride, aluminum nitride, and or silicon oxynitride. The channel of the semiconductor transistor, for example, can be comprised of a P- or N-type semiconductor, as is well known in the art, such as for example, silicon or germanium doped with boron, arsenic, phosphorous, or antimony. A solution in the reaction cavity forms a gate and the components of the sensor are typically placed on a substrate. The source electrode and the drain electrode are typically comprised of conducting materials, as are well know in the art of chip fabrication, such as for example, gold, copper, silver, platinum, nickel, iron, tungsten, aluminum, or titanium. The substrate can be comprised of, for example, silicon, silica, quartz, germanium, or polysilicon. In a further embodiment, the reaction cavity has dimensions of less than about 100 nm. The reaction cavity is used as part of the gate of the transistor. DNA can be immobilized in the reaction cavity by standard methods, such as for example, through biotin-avidin or antibody-antigen binding. Biotin, avidin, antibodies, or antigens can be attached, for example, to an insulating layer comprised of silicon oxide through derivatization of the silica surface with, for example, (3-aminopropyl)triethoxysilane to yield a surface that presents an amine group for molecule attachment. The molecule can be attached by using water-soluble carbodiimide coupling reagents, such as EDC (1-ethyl-3-(3-dimethyl aminopropyl)carbodiimide), which couples carboxylic acid functional groups with amine groups. DNA molecules bearing a corresponding coupling agent can then be attached through the surface through, for example, a biotin-avidin or antibody-antigen interaction. Additionally, acrydite-modified DNA fragments can be attached to a surface modified with thiol groups and amine-modified DNA fragments can be attached to epoxy or aldehyde modified surfaces. In operation, variations in the potential between the solution (the gate) in the reaction cavity and the insulator surface modify the charge distribution in the channel. Changes in the solution, such as changes in charge distribution created by the linearly amplified PPi molecules and protons, can be measured by changes in the conductivity or changes in the capacitance across the channel.

In additional embodiments, the sensor can comprise a carbon nanotube transistor. Carbon nanotube FET devices have been described. See, for example, Star, A., Gabriel, J. P., Bradley, K., Gruner, G., *Nano Letters*, 3:4, 459-463 (2003) and Fritz, J, Cooper, E. B., Gaudet, S., Sorger, P. K., Manalis, S. R., *Proceedings of the National Academy of Sciences*, 99:22, 4984-4989 (2002). In general, carbon nanotubes, such as for example, single-walled carbon nanotubes (SWNTs), that are useful in a FET device, can be made through the chemical vapor deposition of methane onto catalytic iron nanoparticles. Metal evaporation through a mask can be used to create the electrical contacts that form a source and a drain. DNA can be attached to the carbon nanotube transistor, for example, by coating the carbon nanotube with Tween-20™ or polyethylene oxide, which readily adsorb to the surface of the nanotube, activating the Tween-20™ polyethylene oxide-containing polymer with a water-soluble carbodiimide coupling reagent, such as for example, 1,1-carbonyldiimidazole, for conjugation with coupling agents such as biotin, avidin, antigens, or antibodies. DNA molecules having a corresponding coupling agent can then be attached through the surface through, for example, a biotin-avidin or antibody-antigen interaction.

Figure 7:
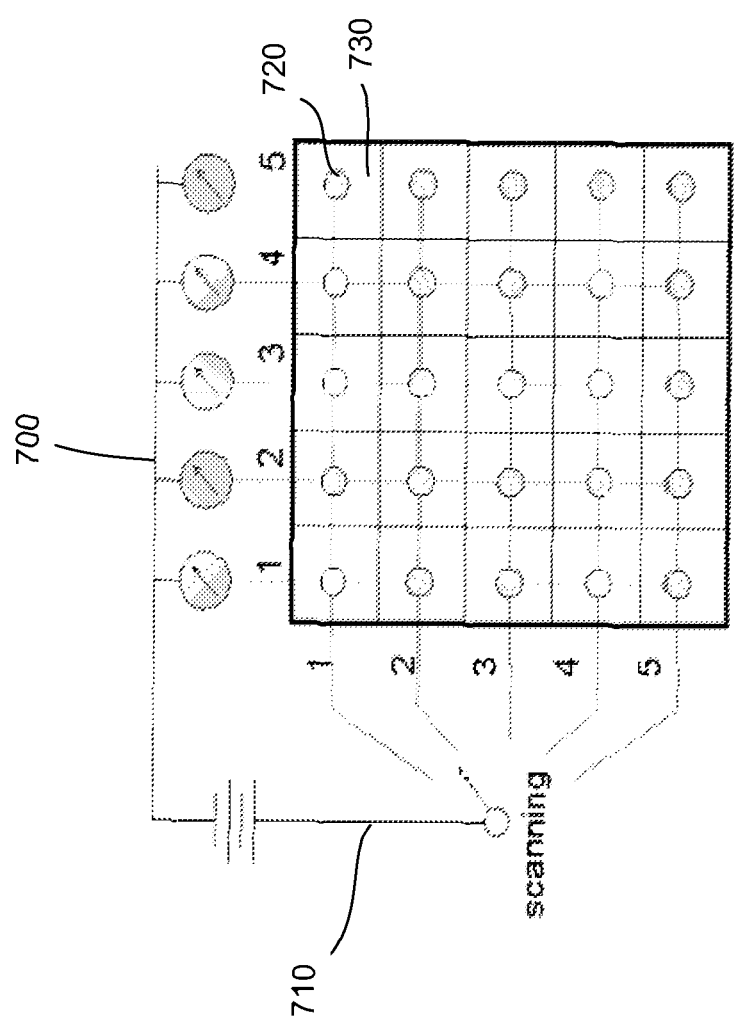
FIG. 7 is a schematic of an array of reaction sites employing field effect transistors that can be used for analyzing nucleic acid sequencing reactions.

Referring now to FIG. 7, an array of electronic sensors is shown. For simplicity, the array is shown having five rows and five columns of sensors, however the invention is not so limited and arrays can be built having a variety of dimensions and numbers of sensor regions. For example, arrays of sensors could be 10×10, 100×100, 1,000×1,000, $10^5 \times 10^5$, and $10^6 \times 10^6$. In FIG. 7, the sensors are depicted as FET sensors that are connected to a source line 700 and a drain line 710. A reaction region 720 is shown in FIG. 7 having circular dimensions, however embodiments of the present invention are not so limited and other shapes and dimensions are possible, such as for example, those having rectangular or other multisided configurations are possible. The reaction region 720 forms part of the transistor gate. The FET sensors 730 can be monitored individually or as a group. The sensor array allows many immobilized DNA molecules to be sequenced simultaneously. The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. Typically, DNA fragments to be immobilized are diluted so that statistically each sensor has one DNA molecule immobilized. Information from FET sensors showing ambiguous results can be disregarded. Sequence information is assembled from the sensors having a single DNA molecule immobilized. Chemical information, such as for example a change in pH or in ionic concentration, from each reaction cavity is sensed independently. Micro and nano-structures on the array can be built to minimize diffusion. For example, wells can be built over each sensor, the sensor array can be placed upside down, well facing down, with the temperature in the down side lower than the chip side, and a low melting point gel (such as low melting point agarose) can be used to make the reaction mixture. Standard silicon and semiconductor processing methods allow a highly integrated sensor array to be made. For example, a 1 cm$^2$ silicon wafer chip can hold as many as 1×10$^8$ sensors that are about 1 µm$^2$ and that present a 0.1 µm opening to the array surface. For example, we calculate that only about 300 sensor arrays would be needed to sequence the whole human genome in about an hour, assuming that such an array having 1×10$^8$ sensors is a 100 M-sensor array, that 10% of the sensors on the array yield single molecule sequencing information, that each immobilized DNA molecule provides 10 bases worth of sequencing information, that 90% of the sequences are overlapped, and assuming conservatively that it takes about 6 minutes to determine sequence information for each base (one test and fill cycle).

Figure 8:
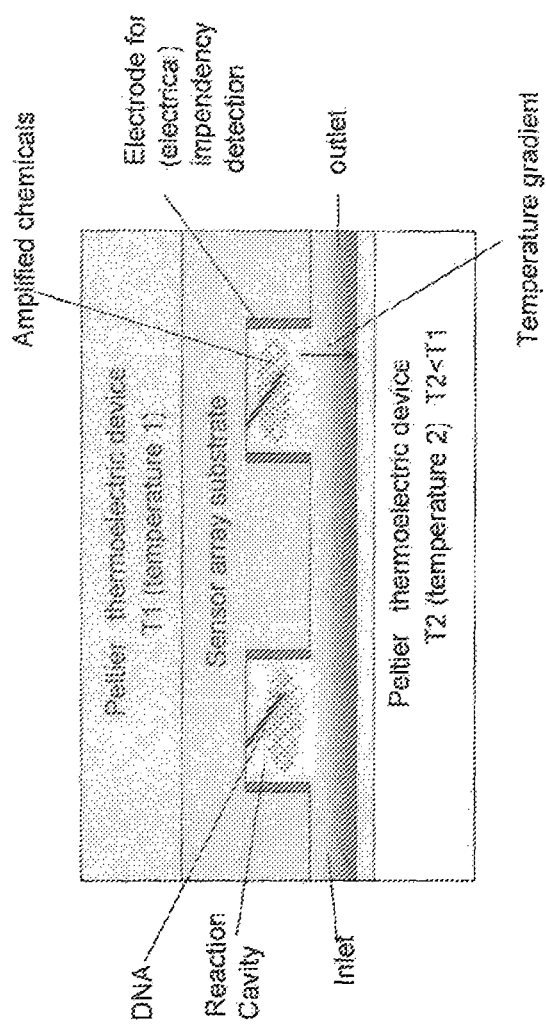
FIG. 8 shows an alternate design for a sensor array that can be used for analyzing nucleic acid sequencing reactions.

Referring now to FIG. 8, an additional design for a sensor array having reaction cavities with downward facing openings is shown. In this array design, a temperature gradient can be used to minimize diffusion from the reaction cavity. The temperature gradient is created, for example, by Peltier thermoelectric devices placed above and below the sensor array. A temperature gradient is maintained so that the temperature below the sensor array (T2) is less than the temperature above the array (T1). Such a temperature gradient reduces convection and thereby limits the diffusion of the amplified reaction products out of the reaction cavity. A temperature gradient, for example, may be created by setting T1 at about 37° C. and T2 to about 35° C. or less (for example, 30° C. or 20° C.). A DNA molecule to be sequenced can be immobilized within the reaction cavity. A substrate to house the sensor array and inlet channels and outlet channels that are for supplying and removing reagents are provided.

Figure 9:
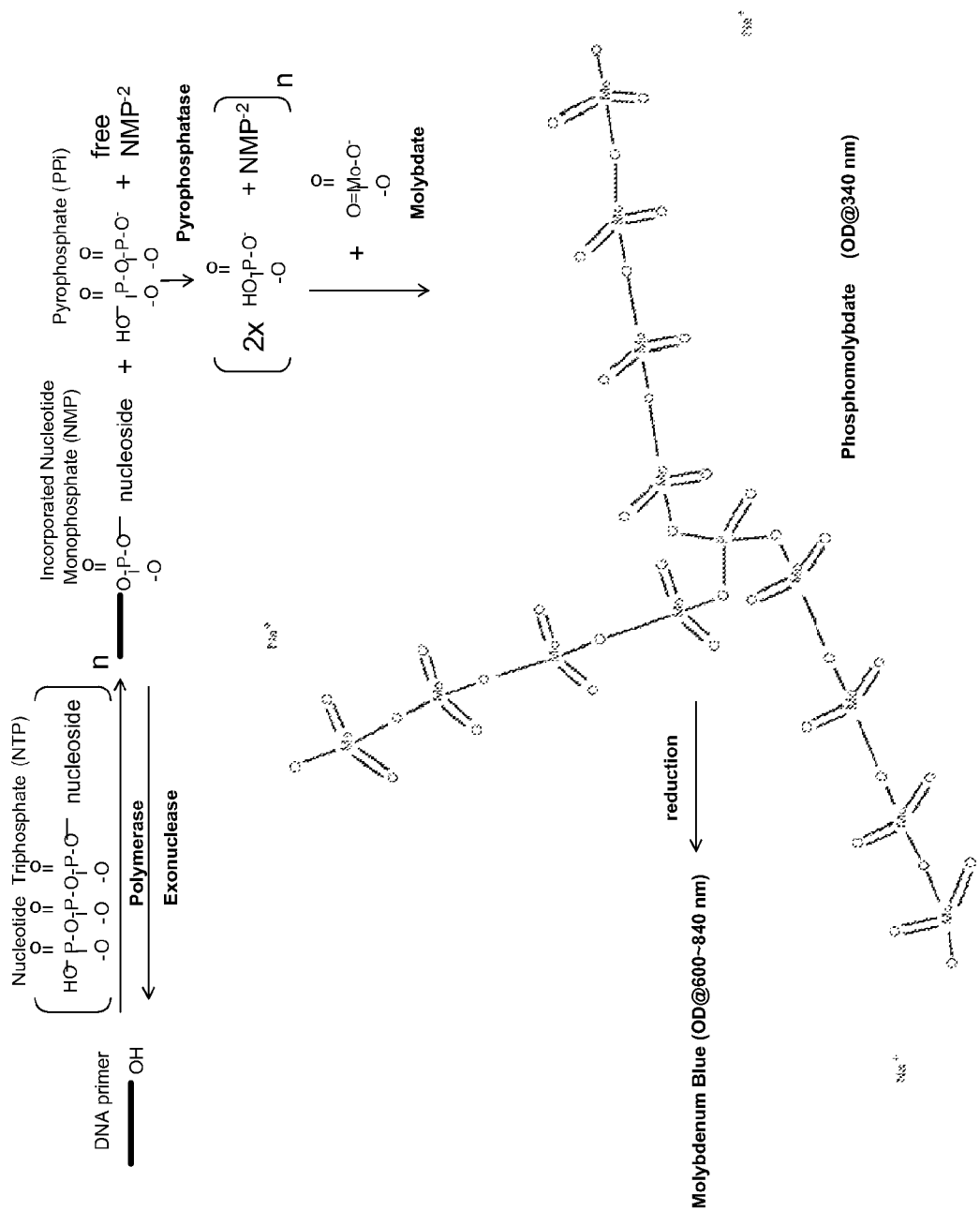
FIG. 9 is a schematic of a method for achieving chemical signal amplification for optical detection of reaction products of a nucleic acid sequencing reaction.

In further embodiments of the present invention, chemical signal amplification can be used in conjunction with optical detection in test and fill sequencing reactions. FIG. 9 provides a reaction scheme whereby the results of a test reaction for DNA sequencing are amplified and converted into a product that can be optically detected. In the initial reaction depicted in FIG. 9, after incorporation of a nucleotide into the DNA primer that matches the base on the DNA to be sequenced through the action of a polymerase enzyme, the nucleotide is then deleted through the action of an exonuclease enzyme. These incorporation and deletion reactions are repeated many times on the same DNA molecule resulting in the consumption of many nucleotide triphosphates (NTP) and the generation of many molecules of phosphate and or pyrophosphate. Phosphate ions generated from test phosphate amplification processes can be reacted, for example, with molybdate ions to form phosphomolybdate. The abundance of phosphomolybdate can be quantified optically by absorbance measurements at about 340 nm. Additionally, phosphomolybdate can be reduced and the resulting molybdenum blue optically detected at about 600 to about 840 nm. Useful reducing agents include, for example, aminonapthosulfonic acid, ascorbic acid, methyl-p-aminophenol sulfate, and ferrous sulfate. Alternatively, pyrophosphate molecules that are amplified from a test reaction can be converted to ATP by ATP sulfurase, and photons emitted by luciferase. See, for example, Ronaghi et al, *Science,* 281, 363-365 (1998). In another embodiment, phosphate and pyrophosphate ions form resorufin in presence of maltose, maltose phosphorylase, glucose oxidase, horse radish peroxidase, and Amplex Red reagent (10-acetyl-3,7-dihydroxyphenoxazine). The resorufin can be detected fluorometrically or spectrophotometrically. See, for example, *The Handbook—A Guide to Fluorescent Probes and Labeling Technologies* Molecular Probes, Section 10.3, available from Invitrogen.

Figure 10:
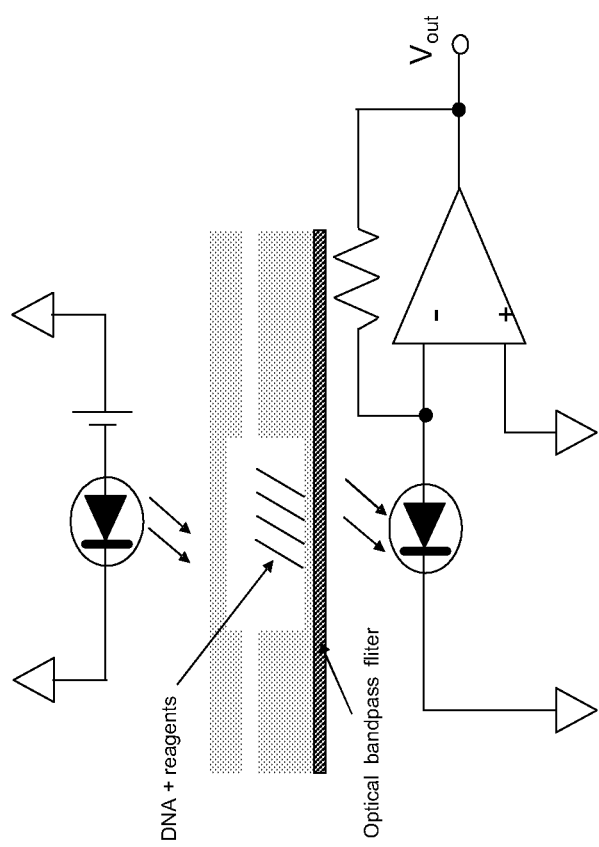
FIG. 10 shows a design for a microfluidic device that can be used for optically detecting the reaction products of a nucleic acid sequencing reaction.

FIG. 10 provides a schematic demonstrating a method by which signals from amplified TAF reactions can be detected optically. Amplified chemical signals from the TAF reactions are converted to an optical signal which is then converted into an electrical signal by an optical detector, for example, a photodiode, CMOS, or CCD detector. In one embodiment, each sensor has a nano-sized reaction cavity in the middle, a light emitting diode on one side, and a photodiode detector on the opposite side. Ideally the cavity is less than about 100 nm, however larger sizes are also useful, such as for example, cavities that have dimensions that are less than about 10 µm in size. Optionally, a bandpass filter, which can be for example, a dielectric filter, can be placed between a photodiode/light emitting diode and the reaction cavity to tailor the wavelength of light transmitted. DNA can be immobilized in the reaction cavity by standard methods, such as streptavidin/biotin binding method. The geometry of each reaction cavity (size, depth, shape and orientation) can be optimized to minimize reaction time. Porous silicon substrates can be used to hold more DNA molecules and accordingly increase the sensitivity. Porous silicon substrates can be used to hold DNA molecules within a smaller area. Optionally, the whole sensor can be packaged in an optically opaque material so that external light does not generate background noise.

Figure 11:
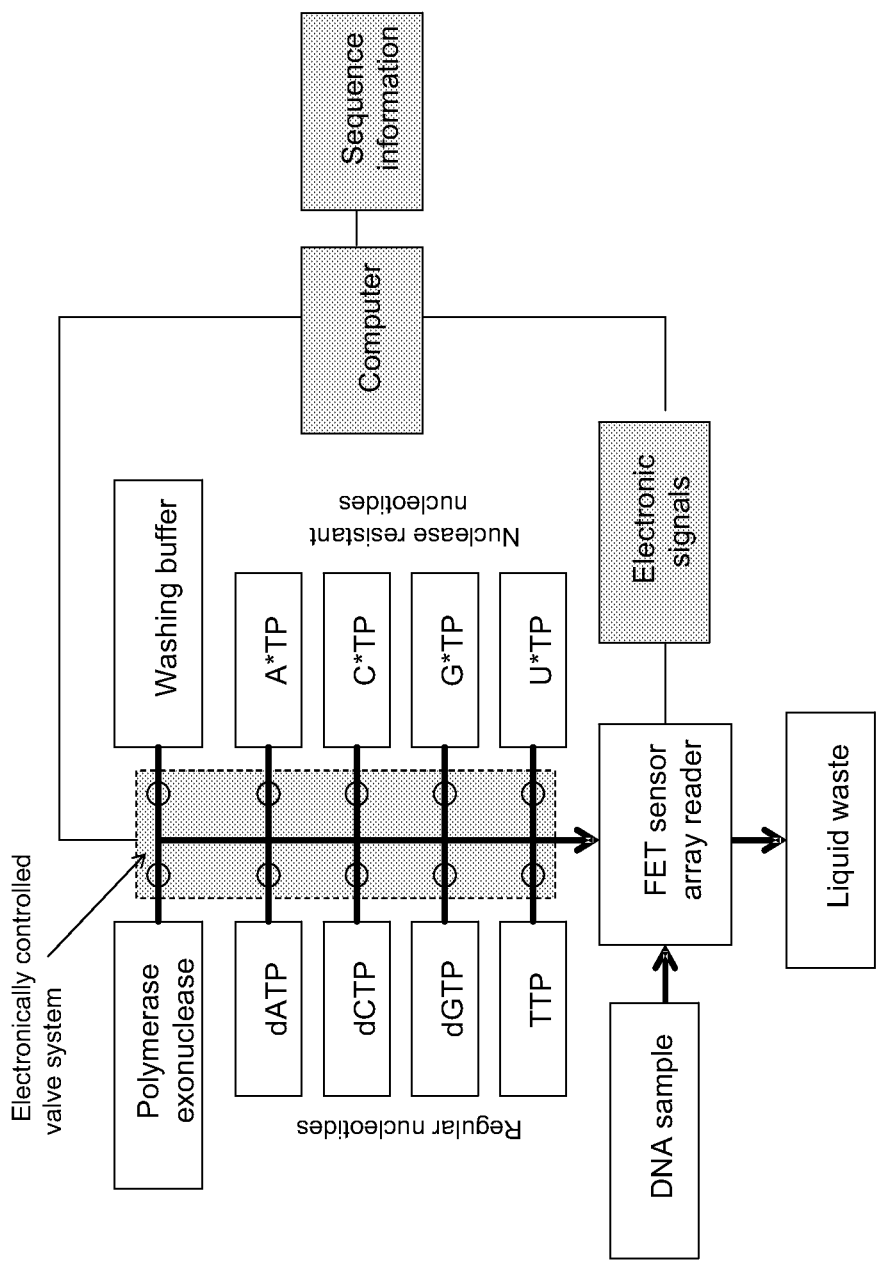
FIG. 11 shows a design for a system that can be used for sequencing nucleic acids.

In FIG. 11, a system that can be used for sequencing is shown. The system contains a fluidic system that regulates reagent delivery and waste removal, a computer that collects and analyzes sequence data, and an array reader that retrieves signals from the array. The array reader can be either an FET sensor array reader or an optical sensor array reader. Reagent delivery and array washing can be controlled, for example with an electronic valve system. Fluid delivery can be controlled by a computer that sends signals to valve drives (not pictured) that control the electronic valve system.

Array compositions may include at least a surface with a plurality of discrete reaction cavities. The size of the array will depend on the end use of the array. Arrays containing from about two to many millions of different discrete reaction cavities can be made. Generally, the array size will depend in part on the size of the surface from which the array is made. Very high density, high density, moderate density, low density, or very low density arrays can be made. Some ranges for very high-density arrays are from about 100,000,000 to about 1,000,000,000 cavities per array. High-density arrays range from about 1,000,000 to about 100,000,000 cavities. Moderate density arrays range from about 10,000 to about 100,000 cavities. Low-density arrays are generally less than 10,000 cavities. Very low-density arrays are less than 1,000 cavities.

The reaction cavities can comprise a pattern or a regular design or configuration or can be randomly distributed. A regular pattern of cavities can be used such that the cavities can be addressed in an X-Y coordinate plane. The surfaces within the cavities can be modified to allow attachment of analytes in individual cavities. In general, reaction cavities are a depression or well in the surface of the substrate that is capable of containing a liquid.

There are numerous suitable methods for patterning an array of nanoscale features on a surface of a substrate. Examples of such suitable methods include lithography methods such as, for example, interferometric lithography (IL), immersion interferometric lithography, electron beam lithography, scanning probe lithography, nanoimprint, extreme ultraviolet lithography, and X-ray lithography, and stamping, etching, microetching, and molding techniques.

The technique used will depend in part on the composition and shape of the substrate. Generally, lithography is a highly specialized printing process used to create detailed patterns on a substrate, such as a silicon wafer. An image containing a desired pattern is projected onto the wafer, which is coated by a thin layer of photosensitive material called resist. The bright parts of the image pattern cause chemical reactions which, in turn, render the resist material soluble, and, thus, dissolve away in a developer liquid, whereas the dark portions of the image remain insoluble. After development, the resist forms a stenciled pattern across the wafer surface, which accurately matches the desired pattern. Finally, the pattern is permanently transferred into the wafer surface, for example by a chemical etchant, which etches those parts of the surface unprotected by the resist.

In various embodiments of the invention, arrays may be incorporated into a larger apparatus and/or system. In certain embodiments, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.*, 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

The electronic components of MEMS may be fabricated using integrated circuit (IC) processes (for example, CMOS, Bipolar, or BICMOS processes). The components may be patterned using photolithographic and etching methods known for computer chip manufacture. The micromechanical components may be fabricated using compatible micromachining processes that selectively etch away parts of the silicon wafer or add new structural layers to form the mechanical and/or electromechanical components.

Basic techniques in chip manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

In some embodiments of the invention, substrates may be connected to various fluid filled compartments, such as microfluidic channels, nanochannels, and or microchannels. These and other components of the apparatus may be formed as a single unit, for example in the form of a chip, such as semiconductor chips and or microcapillary or microfluidic chips. Alternatively, the substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

Techniques for batch fabrication of chips are well known in the fields of computer chip manufacture and or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. See for example, Craighead, *Science*, 290:1532-36, (2000). Various forms of microfabricated chips are commercially available from, for example, Caliper Technologies Inc. (Mountain View, Calif.) and ACLARA BioSciences Inc. (Mountain View, Calif.).

EXAMPLE

Sensor Array Fabrication:

A field effective transistor array having $10^8$ sensors that are pH sensitive is fabricated. The array is a Al—Si—$SiO_2$—$Ta_2O_5$ structure, fabricated from a p-Si wafer with specific receptivity of 1-10 Ohm/cm. A double layer that consists of 65 nm $SiO_2$ and 67 nm $Ta_2O_5$ which is made by thermal oxidation of sputtered Ta (Rolka, D., Poghossian, A., Schoning, M., *Sensors*, 4, 84-94 (2004)). Each sensor in the array is connected to an electronic control board for signal amplification and processing. Wells of $1 \times 1 \times 1$ μm are constructed over each sensor using $SiO_2$ by standard photolithography techniques. The $SiO_2$ surface is modified to present free aldehyde groups through an aldehyde trimethoxysilane process (Lobert, P. E., Hagelsieb, L. M., Pampin, R., Bourgeois, D., Akheyar, A., Flandre, D., Remade, J., *Sensors & Actuators B, Section μTas*, (2002)). Streptavidin is used to coat the well surface surrounding each sensor by sheriff's reaction. Multiple streptavidin molecules are attached to the well wall surface and the uncoated surface is blocked by BSA (bovine serum albumin) molecules. The density of streptavidin molecules on the wall can be adjusted by varying the ratio of streptavidin and BSA. Ideally, the distance between two streptavidin molecules is greater than about 50 nm. The array device is sandwiched between two peltier thermoelectrical coolers, which can be programmed and controlled by a computer.

Fluidic Control:

the sensor array surface is enclosed in a chamber made of plastic, with an inlet and outlet. The inlet is connected to reagent reservoirs and the outlet is connected to a waste chamber. Several reagent reservoirs are kept separate.

Reagents:

major reagent solutions include: 1) Reaction buffer (also used as washing solution): 50 mM NaCl, 10 mM Tris-HCl (pH 7.9), 10 mM $MgCl_2$, 1 mM dithiothreitol, 100 μg/ml BSA; 2) Regular deoxyribonucleotides, dATP, dCTP, dGTP, dTTP, each kept separately at 100 μM in reaction buffer; 3) alpha-phosphorothioate nucleotides, each kept separately at 50 μM in reaction buffer; 4) enzyme mix solution: T4 DNA polymerase at 0.01 unit/μl (with DNA polymerase activity and strong 3' to 5' exonuclease activity in the same enzyme) and pyrophosphatase at 0.001 unit/μl in reaction buffer.

DNA Sample Preparation:

The sensor chip is a universal chip for DNA sequence detection, depending on DNA sample used. In this example, bacterial contamination in water is to be determined. A sample of water to be tested (1 L) is concentrated using a 0.22 μm filter. DNA is extracted from the sample with a DNA purification kit (Qiagen), and digested to an average length of 100 bp by DNase I digestion. The 3' end of the DNA fragments are modified by biotin labeled alpha-phosphorothioate dideoxyribonucleotides in a terminal transferase reaction, in which dATP and the biotin nucleotide is in a 30:1 ratio. The modified DNA fragments will have a poly A tail, terminated with a nuclease resistant biotin-labeled nucleotide.

DNA Template Immobilization:

About 1 pg of the modified DNA fragments (about $1 \times 10^8$ copies) is added to the chip so that the DNA fragments are captured to the sensor well (1 fragment/sensor on average; the distance between 2 streptavidin molecules are longer than the length of 100 bp DNA,) by biotin-strepavidin binding. The capture double-stranded DNA molecules are denatured by washing the chip with an alkaline solution (50 mM, NaOH). The chip is neutralized and nuclease resistant oligo dT primers (a set of 3 each terminated with A, C, and G, respectively) are hybridized to the immobilized single-stranded DNA molecules.

Sequence Detection Operation:

After immobilizing DNA and loading the reagents into the system (all reagents and chips are set at 4° C.), the sequence detection reaction can start. 1) The chip is washed and primed with the reaction buffer; 2) one of the 4 regular nucleotides (dCTP, for example) is mixed with the enzyme solution in 1:1 volume; 3) the mixture is introduce to the chip to replace the priming buffer (all at 4° C.), some mixing in the chip is necessary to ensure all sensors received the reagent at the same concentration; 4) the chip concentration is raised to 37° C. and for 3 min.; 5) a signal is recorded from each sensor; 6) the sensor is cleaned with reaction buffer; 7) the tested base (dCTP) is filled with the same base (alpha-phosphorothioate dCTP) for 2 min.; 8) the chip is cleaned with reaction buffer; 9) the preceding steps are repeated for each of the other bases; and 10) the whole reaction cycle (steps 1-9) is repeated.

Data Analysis:

Recorded data from each sensor is analyzed. Sensors with no information or unidentifiable information from each step are ignored for further data analysis. The rest of the data is analyzed as follows: the frequency of given sequences is calculated, the sequence information is analyzed based on sequence alignment based on fragments of similar frequency to generate longer fragment information, and the assembled sequence is searched against a database of know sequences.

We claim:

1. A method comprising,
providing a first set of reactants to a DNA molecule to be sequenced with a DNA oligo hybridized thereto, the DNA oligo comprising at 3'-end of the DNA oligo a first nuclease-resistant nucleotide or a first nuclease-resistant nucleotide analog,
performing repeated nucleotide addition and excision reactions without cleavage of the first nuclease-resistant nucleotide or the first nuclease-resistant nucleotide analog;
identifying the base of the DNA molecule to be sequenced immediately upstream from the base of the DNA molecule complementary to the first nuclease-resistant nucleotide by monitoring increases in reaction;
attaching a second nuclease-resistant blocking nucleotide or a second nuclease-resistant blocking nucleotide analog to the 3'-end of the DNA oligo, the second nuclease-resistant blocking nucleotide or the second nuclease-resistant blocking nucleotide analog being complementary to the identified base.

2. The method of claim 1, wherein the first set of reactants comprise a polymerase.

3. The method of claim 2, wherein the polymerase is Klenow (exo-).

4. The method of claim 1, wherein the first set of reactants comprises an exonuclease.

5. The method of claim 4, wherein the exonuclease is exonuclease III.

6. The method of claim 1, wherein the first nuclease-resistant blocking nucleoside comprises alpha-thiophosphate.

7. The method of claim 1, wherein the nucleotide is a naturally occurring nucleotide or an analog thereof.

8. The method of claim 1, wherein the nucleotide is labeled.

9. The method of claim 1, further comprising deblocking the second nuclease-resistant blocking nucleotide or the second nuclease-resistant blocking nucleotide analog.

10. The method of claim 1, wherein the first set of reactants comprises only one type of nucleobase selected from the group consisting of adenine, cytosine, guanine, thymine and uracil.

11. A method comprising,
providing a first set of reactants to a DNA molecule to be sequenced with a DNA oligo hybridized thereto, the DNA oligo comprising at 3'-end of the DNA oligo a first nuclease-resistant nucleotide or a first nuclease-resistant nucleotide analog,
performing repeated nucleotide addition and excision reactions without cleavage of the first nuclease-resistant nucleotide or the first nuclease-resistant nucleotide analog;
identifying the base of the DNA molecule to be sequenced immediately upstream from the base of the DNA molecule complementary to the first nuclease-resistant nucleotide by monitoring increases in reaction;
attaching a second nuclease-resistant blocking nucleotide or a second nuclease-resistant blocking nucleotide analog to the 3'-end of the DNA oligo, the second nuclease-resistant blocking nucleotide or the second nuclease-resistant blocking nucleotide analog being complementary to the identified base,
further comprising:
providing an array comprised of a plurality of reaction regions, each of the reaction regions comprising a reaction cavity having a surface and coupled electronic sensors for detecting chemical reaction product changes in a solution;
attaching DNA molecules to be sequenced to the surface so that statistically only one DNA molecule to be sequenced is attached in each reaction cavity, and
deblocking the nuclease-resistant blocking nucleotide after terminating the primer DNA molecule with an alpha-thiophosphate blocking nuclease-resistant nucleotide that has been identified as complementary to a base of the attached DNA molecule.

12. The method of claim 11, wherein the sensor comprises a single walled carbon nanotube that is capable of acting as field effect transistor.

13. A method comprising,
providing a first set of reactants to a DNA molecule to be sequenced with a DNA oligo hybridized thereto, the DNA oligo comprising at 3'-end of the DNA oligo a first nuclease-resistant nucleotide or a first nuclease-resistant nucleotide analog, performing repeated nucleotide addition and excision reactions without cleavage of the first nuclease-resistant nucleotide or the first nuclease-resistant nucleotide analog;

identifying the base of the DNA molecule to be sequenced immediately upstream from the base of the DNA molecule complementary to the first nuclease-resistant nucleotide by monitoring increases in reaction;

attaching a second nuclease-resistant blocking nucleotide or a second nuclease-resistant blocking nucleotide analog to the 3'-end of the DNA oligo, the second nuclease-resistant blocking nucleotide or the second nuclease-resistant blocking nucleotide analog being complementary to the identified base, further comprising:

providing an array comprised of a plurality of reaction regions, each of the reaction regions comprising a reaction cavity having a surface and coupled electronic sensors for detecting chemical reaction product changes in a solution; and attaching DNA molecules to be sequenced to the surface so that statistically only one DNA molecule to be sequenced is attached in each reaction cavity.

14. The method of claim 13, wherein the sensor comprises a single walled carbon nanotube that is capable of acting as field effect transistor.

* * * * *